United States Patent
Lynch et al.

(10) Patent No.: US 6,783,544 B2
(45) Date of Patent: *Aug. 31, 2004

(54) STENT DEVICE AND METHOD FOR TREATING GLAUCOMA

(75) Inventors: Mary G. Lynch, Atlanta, GA (US); Reay H. Brown, Atlanta, GA (US)

(73) Assignee: GMP Vision Solutions, Inc., Ft. Lauderdale, FL (US)

(*) Notice: Subject to any disclaimer, the term of this patent is extended or adjusted under 35 U.S.C. 154(b) by 49 days.

This patent is subject to a terminal disclaimer.

(21) Appl. No.: 10/269,636

(22) Filed: Oct. 11, 2002

(65) Prior Publication Data

US 2003/0069637 A1 Apr. 10, 2003

Related U.S. Application Data

(63) Continuation of application No. 09/557,849, filed on Apr. 26, 2000, now Pat. No. 6,464,724.
(60) Provisional application No. 60/131,030, filed on Apr. 26, 1999.

(51) Int. Cl.$^7$ .................................................. A61F 2/14
(52) U.S. Cl. ............................... 623/4.1; 623/1.15
(58) Field of Search ............................ 623/4.1, 1.15, 623/11.11, 1.1, 1.35; 604/8, 264, 523, 284

(56) References Cited

U.S. PATENT DOCUMENTS

| | | | |
|---|---|---|---|
| 3,159,161 A | 12/1964 | Ness | |
| 3,788,327 A | 1/1974 | Donowitz et al. | 128/350 |
| 4,037,604 A | 7/1977 | Newkirk | 128/350 |
| 4,175,563 A | 11/1979 | Arenberg et al. | 128/350 |
| 4,402,681 A | 9/1983 | Haas et al. | 604/9 |
| 4,428,746 A | 1/1984 | Mendez | 604/8 |
| 4,457,757 A | 7/1984 | Molteno | 604/294 |
| 4,501,274 A | 2/1985 | Skjaerpe | 128/305 |
| 4,521,210 A | 6/1985 | Wong | 604/8 |
| 4,554,918 A | 11/1985 | White | 604/10 |
| 4,604,087 A | 8/1986 | Joseph | 604/9 |
| 4,632,842 A | 12/1986 | Karwoski et al. | 427/2 |
| 4,634,418 A | 1/1987 | Binder | 604/8 |
| 4,718,907 A | 1/1988 | Karwoski et al. | 623/12 |
| 4,733,665 A | 3/1988 | Palmaz | 128/343 |
| 4,750,901 A | 6/1988 | Molteno | 604/8 |
| 4,787,885 A | 11/1988 | Binder | 604/8 |
| 4,846,172 A | 7/1989 | Berlin | 128/303.1 |
| 4,863,457 A | 9/1989 | Lee | 604/891 |
| 4,886,488 A | 12/1989 | White | 604/9 |
| 4,900,300 A | 2/1990 | Lee | 604/22 |
| 4,936,825 A | 6/1990 | Ungerleider | 604/8 |
| 4,946,436 A | 8/1990 | Smith | 604/8 |
| 4,968,296 A | 11/1990 | Ritch et al. | 604/8 |
| 5,041,081 A | 8/1991 | Odrich | 604/9 |

(List continued on next page.)

FOREIGN PATENT DOCUMENTS

| | | |
|---|---|---|
| AU | 200072059 | 7/2001 |
| CA | 2244646 | 2/1999 |
| CH | 92111244 | 7/1993 |

(List continued on next page.)

OTHER PUBLICATIONS

Allen D. Beck and Mary G. Lynch, "360° Trabeculotomy for Primary Congenital Glaucoma," *Arch. Ophthalmol.* 113 (Sep. 1995), pp. 1200–1202.

(List continued on next page.)

*Primary Examiner*—Edward K. Look
*Assistant Examiner*—Richard A. Edgar
(74) *Attorney, Agent, or Firm*—Sutherland Asbill & Brennan LLP

(57) ABSTRACT

Stent devices and a method for continuously facilitating the flow of aqueous humor through Schlemm's canal where post-operative patency can be maintained with an indwelling stent device. The stent devices provide uni- or bi-directional flow of aqueous humor within and through Schlemm's canal.

9 Claims, 3 Drawing Sheets

U.S. PATENT DOCUMENTS

| | | | |
|---|---|---|---|
| 5,073,163 A | 12/1991 | Lippman | 604/9 |
| 5,092,837 A | 3/1992 | Ritch et al. | 604/8 |
| 5,095,887 A | 3/1992 | Leon et al. | 128/4 |
| 5,127,901 A | 7/1992 | Odrich | 604/9 |
| 5,129,895 A | 7/1992 | Vassiliadis et al. | 606/6 |
| 5,171,213 A | 12/1992 | Price, Jr. | 604/9 |
| 5,178,604 A | 1/1993 | Baerveldt et al. | 604/8 |
| 5,180,362 A | 1/1993 | Worst | 604/8 |
| 5,246,451 A | 9/1993 | Trescony et al. | 623/1 |
| 5,300,020 A | 4/1994 | L'Esperance, Jr. | 604/9 |
| 5,318,513 A | 6/1994 | Leib et al. | 604/8 |
| 5,334,137 A | 8/1994 | Freeman | 604/8 |
| 5,338,291 A | 8/1994 | Speckman et al. | 604/9 |
| 5,346,464 A | 9/1994 | Camras | 604/9 |
| 5,360,399 A | 11/1994 | Stegmann | 604/49 |
| 5,370,607 A | 12/1994 | Memmen | 604/8 |
| 5,370,641 A | 12/1994 | O'Donnell, Jr. | 606/4 |
| 5,372,577 A | 12/1994 | Ungerleider | 604/8 |
| 5,397,300 A | 3/1995 | Baerveldt et al. | 604/8 |
| 5,433,701 A | 7/1995 | Rubinstein | 604/8 |
| 5,454,796 A | 10/1995 | Krupin | 604/294 |
| 5,476,445 A | 12/1995 | Baerveldt et al. | 604/8 |
| 5,486,165 A | 1/1996 | Stegmann | 609/294 |
| 5,520,631 A | 5/1996 | Nordquist et al. | 604/8 |
| 5,557,453 A | 9/1996 | Schalz et al. | 359/376 |
| 5,558,629 A | 9/1996 | Baerveldt et al. | 609/8 |
| 5,558,630 A | 9/1996 | Fisher | 604/8 |
| RE35,390 E | 12/1996 | Smith | 604/8 |
| 5,601,094 A | 2/1997 | Reiss | 128/899 |
| 5,601,549 A | 2/1997 | Miyagi | 606/6 |
| 5,626,558 A | 5/1997 | Suson | 604/8 |
| 5,626,559 A | 5/1997 | Solomon | 604/9 |
| 5,639,278 A | 6/1997 | Dereume et al. | 623/1 |
| 5,651,783 A | 7/1997 | Reynard | 606/4 |
| 5,670,161 A | 9/1997 | Healy et al. | 424/426 |
| 5,676,679 A | 10/1997 | Simon et al. | 606/170 |
| 5,681,275 A | 10/1997 | Ahmed | 604/9 |
| 5,702,414 A | 12/1997 | Richter et al. | 606/166 |
| 5,702,419 A | 12/1997 | Berry et al. | 606/198 |
| 5,704,907 A | 1/1998 | Nordquist et al. | 604/8 |
| 5,713,844 A | 2/1998 | Peyman | 604/9 |
| 5,723,005 A | 3/1998 | Herrick | 623/4 |
| 5,741,333 A | 4/1998 | Frid | 623/12 |
| 5,743,868 A | 4/1998 | Brown et al. | 604/8 |
| 5,752,928 A | 5/1998 | de Roulhac et al. | 604/8 |
| 5,766,243 A | 6/1998 | Christensen et al. | 623/4 |
| 5,785,674 A | 7/1998 | Mateen | 604/9 |
| 5,807,302 A | 9/1998 | Wandel | 604/8 |
| 5,810,870 A | 9/1998 | Myers et al. | 606/198 |
| 5,830,171 A | 11/1998 | Wallace | 604/8 |
| 5,836,939 A | 11/1998 | Negus et al. | 606/11 |
| 5,865,831 A | 2/1999 | Cozean et al. | 606/6 |
| 5,868,697 A | 2/1999 | Richter et al. | 604/8 |
| 5,879,319 A | 3/1999 | Pynson et al. | 604/8 |
| 5,882,327 A | 3/1999 | Jacob | 604/8 |
| 5,893,837 A | 4/1999 | Eagles et al. | 604/9 |
| 5,968,058 A | 10/1999 | Richter et al. | 606/166 |
| 5,981,598 A | 11/1999 | Tatton | 514/549 |
| 6,004,302 A | 12/1999 | Brierley | 604/264 |
| 6,007,510 A | 12/1999 | Nigam | 604/8 |
| 6,007,511 A | 12/1999 | Prywes | 604/9 |
| 6,033,434 A | 3/2000 | Borghi | 623/1 |
| 6,045,557 A | 4/2000 | White et al. | 606/108 |
| 6,050,970 A | 4/2000 | Baerveldt | 604/28 |
| 6,059,772 A | 5/2000 | Hsia et al. | 606/4 |
| 6,059,812 A | 5/2000 | Clerc et al. | 606/198 |
| 6,063,116 A | 5/2000 | Kelleher | 623/4 |
| 6,063,396 A | 5/2000 | Kelleher | 424/428 |
| 6,071,286 A | 6/2000 | Mawad | 606/108 |
| 6,077,299 A | 6/2000 | Adelberg et al. | 623/24 |
| 6,102,045 A | 8/2000 | Nordquist et al. | 128/898 |
| 6,142,990 A | 11/2000 | Burk | 606/6 |
| 6,168,575 B1 | 1/2001 | Soltanpour | 604/9 |
| 6,174,305 B1 | 1/2001 | Mikus et al. | 604/500 |
| 6,193,656 B1 | 2/2001 | Jeffries et al. | 600/398 |
| 6,197,056 B1 | 3/2001 | Schachar | 623/4.1 |
| 6,228,873 B1 | 5/2001 | Brandt et al. | 514/347 |
| 6,231,597 B1 | 5/2001 | Deem et al. | 623/1.12 |
| 6,241,721 B1 | 6/2001 | Cozean et al. | 606/6 |
| 6,266,182 B1 | 7/2001 | Morita | 359/383 |
| 6,268,398 B1 | 7/2001 | Ghosh et al. | 514/634 |
| 6,342,058 B1 | 1/2002 | Portney | 606/107 |
| 6,375,642 B1 | 4/2002 | Grieshaber et al. | 604/294 |
| 6,464,724 B1 * | 10/2002 | Lynch et al. | 623/4.1 |
| 6,494,857 B1 * | 12/2002 | Neuhann | 604/8 |
| 6,533,768 B1 | 3/2003 | Hill | 604/521 |
| 2002/0013546 A1 | 1/2002 | Grieshaber et al. | 604/28 |
| 2002/0026200 A1 | 2/2002 | Savage | 606/108 |
| 2002/0072673 A1 | 6/2002 | Yamamoto et al. | 600/452 |
| 2002/0082591 A1 | 6/2002 | Haefliger | 606/6 |
| 2002/0133168 A1 | 9/2002 | Smedley et al. | 606/108 |
| 2002/0143284 A1 | 10/2002 | Tu et al. | 604/9 |
| 2002/0165478 A1 | 11/2002 | Gharib et al. | 604/8 |
| 2002/0169130 A1 | 11/2002 | Tu et al. | 514/12 |
| 2002/0188308 A1 | 12/2002 | Tu et al. | 606/167 |

FOREIGN PATENT DOCUMENTS

| | | |
|---|---|---|
| DE | 198 40 047 | 3/2000 |
| EP | 0 881 055 | 2/1998 |
| EP | 0 858 788 | 8/1998 |
| EP | 0 898 947 | 3/1999 |
| EP | 1114627 | 7/2001 |
| FR | 2710269 | 3/1995 |
| JP | 11123205 | 5/1999 |
| WO | 89/00869 | 2/1989 |
| WO | 92/00112 | 1/1992 |
| WO | 92/19294 | 11/1992 |
| WO | 96/36377 | 11/1996 |
| WO | 98/23237 | 6/1998 |
| WO | 98/30181 | 7/1998 |
| WO | 98/35639 | 8/1998 |
| WO | 99/26567 | 6/1999 |
| WO | 99/30641 | 6/1999 |
| WO | 99/38470 | 8/1999 |
| WO | 00/13627 | 3/2000 |
| WO | 00/64389 | 11/2000 |
| WO | 00/64390 | 11/2000 |
| WO | 00/64391 | 11/2000 |
| WO | 00/64393 | 11/2000 |
| WO | 00/72788 | 12/2000 |
| WO | 01/41685 | 6/2001 |
| WO | 01/50943 | 7/2001 |
| WO | 01/78656 | 10/2001 |
| WO | 01/78631 A2 A3 | 10/2001 |
| WO | 01/97727 | 12/2001 |
| WO | 02/36052 | 5/2002 |
| WO | 02/056758 | 7/2002 |
| WO | 02/074052 | 9/2002 |
| WO | 02/080811 | 10/2002 |

OTHER PUBLICATIONS

Grant, W.M., "Further studies on facility of flow through the trabecular meshwork", A.M.A. Archives of Ophthalmology, Oct. 1958, vol. 60, pp. 523–533.

Hill, et al., "Free–electron laser (FEL) Ablation of Ocular Tissues", Laser Med Sci. 1998, vol. 13:219–226.

Hill, et al., "Laser trabecular ablation (LTA)", Laser in Surgery and Medicine, 1991, vol. 11, pp. 341–346.

Hoerauf, et al., "Slit–lamp–adapted optical coherence tomography of the anterior segment", Graefe's Arch Clin. Exp. Ophthalmol., 2000, vol. 238: pp. 8–18.

Jacobi, et al., Goniocurettage for removing trabecular meshwork: Clinical Results of a New Surgical Technique in Advanced Chronic Open–Angle Glaucoma, American Journal of Ophthalmology, May 1999, pp. 505–510.

Jacobi, et al., "Bimanual trabecular aspiratio in pseudoexfoliation glaucoma", Ophthalmology, 1998, vol. 105, No. 5, May 1998, pp. 886–894.

Jacobi, et al., "Microendoscopic trabecular surgery in glaucoma management", Ophthalmology, 1999, vol. 106, No. 3, pp. 538–544.

Johnstone, et al., "Cylindrical Tubular Structures Spanning From Trabecular Meshwork Across SC: Laboratory Studies With SEM, TEM & Tracers Correlated With Clinical Findings", American Glaucoma Society, $12^{th}$ Annual Meeting, , p. 39.

Johnson, M.C., et al. "The Role of Schlemm's Canal in Aqueous Outflow from the Human Eye", Investigative Ophthalmology & Visual Science, vol. 24, No. 3, Mar. 1983, pp. 320–325.

Katz, L. Jay, "A call for innovative operations for glaucoma", Arch Ophthalmology, Mar. 2000, vol. 118, pp. 412–413.

Luntz, et al., "Trabeculotomy ab externo and trabeculectomy in congential and adult–onset glaucoma", American Journal of Ophthalmology, Feb. 1977, vol. 83,. No. 2, pp. 174–179.

Matsumoto, et al., "Trabecular Meshwork Phagocytosis in Glaucomatous Eyes", Ophthalmologica 1997, vol. 211, pp. 147–152.

Nickells, Robert W., "Apoptosis of retinal ganglion cells in glaucoma: an update of the molecular pathways involved in cell death", Survey of Ophthalmology, vol. 43, Supplement 1, Jun. 1999, pp. S151–S161.

Putney, et al., "Intracellular Cl regulates Na–K–Cl cotransport activity in human trabecular meshowrk cells", 1999 American Physiological Society, Sep. 1999, pp. C373–C383.

Radhakrishnan, et al., "Real–time optical coherence tomography of the anterior segment at 1310 nm", Arch Ophthalmology, Aug. 2001, vol. 119, pp. 1179–1185.

Rohen, Johannes W., "Anatomy of the aqueous outflow channels", Grune & Stratton, Harcourt Brace Jovanovich Publishers, Copyright 1986, edited by J.E. Cairns, Glaucoma, vol. 1, Chapter 14, pp. 277–296.

Schwartz, et al., "Trabecular surgery" Arch Ophthalmol, vol. 92, Aug. 1974, pp. 134–138.

Shields, et al., "Aqueous humor dynamics", A Study Guide for Glaucoma, Williams & Wilkins, copyright 1982, pp. 6–43.

Spiegel, D., "Surgical Glaucoma Therapy" in Benefits and Risk of Ophthalmological Therapy (Kampik & Grehn, Eds.) Ch. 7 (Germany 1998).

Strange, Kevin, "Cellular and molecular physiology of cell volume regulation", Library of Congress Cataloging in–Publication Data, CRC Press, Inc., Copyright 1993, pp. 311–321.

Tatton, W.G., "Apoptotic mechanisms in neurodegeneration: possible relevance to glaucoma", European Journal of Ophthalmology 1999, Jan.–Mar., vol. 9, Supplement 1, pp. S22–S29.

Tatton, et al., "Maintaining mitochondrial membrane impermeability: an opportunity for new therapy in glaucoma", Survey of Ophthalmology, vol. 45, Supplement 3, May 2001, pp. S277–S283.

Tripathi et al., "Functional Anatomy of the Anterior Chamber Angle", Biomedical Foundations of Ophthalmology, vol. 1, Chapter 10, pp. 1–74; Edited by Thomas Dune and Edward Jaeger, Revised Edition 1983,—Harper & Row, Publishers.

Wilson, Ellen D., "Implants offer choices for glaucoma surgeons", EW Glaucoma, Oct. 11, 1999, website "http://www.eyeorld.org/sep99/999p60.asp."

Buskirk, E. Michael et al., "Lens Depression and Aqueous Outflow in Enucleated Primate Eyes", American Journal of Ophthalmology, vol. 76, No. 5, Nov. 1973, pp. 632–640.

Buskirk, E. Michael, "Trabeculotomy in the immature, enucleated human eye", Invest. Ophthalmol. Visual Sci., vol. 16, No. 1, Jan. 1977, pp. 63–66.

Demailly, P., et al., "Non–penetrating deep sclerectomy combined with a collagen implant in primary open–angle glaucoma. Medium–term retrospective results", J. Fr. Ophthalmol., vol. 19, No. 11, 1996, pp. 659–666. (Abstract only).

Fine, Ben S., et al., "A Clinicopathologic Study of Four Cases of Primary Open–Angle Glaucoma Compared to Normal Eyes", American Journal of Ophthalmolgy, vol. 91, No. 1, 1981, pp. 88–105.

Gharagozloo, N. Ziai, et al., "Unilateral exfoliation syndrome without glaucoma—a comparison of aqueous dynamica between affected and normal eyes", Glaucoma Paper Presentaon, (abstract only—not dated).

Grierson, I., et al., "Age–related Changes in the Canal of Schlemm", Exp. Eye Res., (1984) 39, pp. 505–512.

Hamard, P., et al., "Deep nonpenetrating sclerectomy and open angle glaucoma. Intermediate results from the first operated patients", J. Fr. Ophthalmol, vol. 22 (j), Feb. 1999, pp. 25–31, (abstract only).

"Improving the flow: A survey of available implants", EW Practice Management, Oct. 11, 1999, website "http://www.eyeworld.org/tooltime/999inserts.asp".

Johnson, M.C., et al, "The Role of Schlemm's Canal in Aqueous Outflow from the Human Eye", Investigative Ophthalmology & Visual Science, vol. 24, No. 3, Mar. 1983, pp. 320–325.

Karlen, M.E., et al., "Deep sclerectomy with collagen implant: medium term results", Br. J. Ophthalmol. vol. 83, No. 1, Jan. 1999, pp. 6–11, (abstract only).

Mermoud, A., et al., "Comparision of deep sclerectomy with collagen implant and trabeculectomy in open–angle glaucoma", J. Cataract Refract. Surg., vol. 25, No. 3, Mar. 1999, pp. 323–331, (abstract only).

McMenamin, Paul G., et al., "Age–related Changes in the Human Outflow Apparatus", Ophthalmology, vol. 93, No. 2., Feb. 1986, pp. 194–209.

Moses, Robert A. et al., "Blood Reflux in Schlemm's Canal", Arch Ophtalmol., vol. 97, Jul. 1979, pp. 1307–1310.

Moses, Robert A., "Circumferential Flow in Schlemm's Canal", American Journal of Ophthalmology, vol. 88, No. 3, Part II, Sep. 1979, pp. 585–591.

Robinson, James C., et al., "Superior Cervical Ganglionectomy: Effects on Aqueous Human Flow in the Cynomolgus Monkey", Glaucoma Paper Presentation, (abstract only—not dated).

Samalonis, Lisa B., "New Horizons in the surgical treatment of glaucoma", EW Glaucoma, Oct. 11, 1999, website "http://www.eyeworld.org/sep99/999p62.asp".

Shields, M. Bruce, Textbook of Glaucoma, Fourth Ed., Williams & Wilkins Publishers, 1998, pp. 5–31.

Spiegel, Detlev, et al., "Schlemm's Canal Implant: A New Method to Lower Intraocular Pressure in Patients with POAG", Ophthalmic Surgery and Lasers, vol. 30, No. 6, Jun. 1999, pp. 492–494.

Spiegel, D., "Surgical Glaucoma Therapy" in Benefits and Risks of Ophthalmological Therapy (Kampik & Grehn, Eds.) Ch. 7 (Germany 1998).

Tripathi et al., "Functional Anatomy of the Anterior Chamber Angle", Biomedical Foundations of Ophthalmology, vol. 1, Chapter 10, pp. 1–74; Edited by Thomas Dune and Edward Jaeger, Revised Edition 1983,—Haper & Row, Publishers.

U.S. Clinical Wick Trials, Oct. 11, 1999, website http://www.cornea.org/us.htm. Allingham, R.R., et al., "Morphometric Analysis of Schlemm's Canal in Normal and Glaucomatous Human Eyes", Glaucoma Paper Presentation, (abstract only—not dated).

Welsh, N.H., et al., "The 'deroofing' of Schlemm's canal in patients with open–angle glaucoma through placement of a collagen drainage device", Ophthalmic Surg. Lasers, vol. 29, No. 3, Mar. 1998, pp. 216–226.

Wilson, Ellen D., "Implants offers choices for glaucoma surgeons", EW Glaucoma, Oct. 11, 1999, website "http://www.eyeorld.org/sep99/999p60.asp".

* cited by examiner

STENT DEVICE AND METHOD FOR TREATING GLAUCOMA

CROSS-REFERENCE TO RELATED APPLICATIONS

This application is a continuation of U.S. patent Ser. No. 09/557,849, filed Apr. 26, 2000, now U.S. Pat. No. 6,464,724, which claims the benefit of U.S. Provisional Application No. 60/131,030, filed Apr. 26, 1999.

GOVERNMENT LICENSE

The U.S. Government has reserved a nonexclusive, irrevocable, royalty-free license in the invention with power to grant licenses for all governmental purposes.

TECHNICAL FIELD

The present invention is generally directed to a surgical treatment for glaucoma, and relates more particularly to a device and method for continuously maintaining the patency of Schlemm's canal with a trough-like, indwelling stent which can be surgically placed to traverse at least a portion of the circumference of the canal and to facilitate the drainage of aqueous humor therethrough.

BACKGROUND OF THE INVENTION

Glaucoma is a significant public health problem, because glaucoma is a major cause of blindness. The blindness that results from glaucoma involves both central and peripheral vision and has a major impact on an individual's ability to lead an independent life.

Glaucoma is an optic neuropathy (a disorder of the optic nerve) that usually occurs in the setting of an elevated intraocular pressure. The pressure within the eye increases and this is associated with changes in the appearance ("cupping") and function ("blind spots" in the visual field) of the optic nerve. If the pressure remains high enough for a long enough period of time, total vision loss occurs. High pressure develops in an eye because of an internal fluid imbalance.

The eye is a hollow structure that contains a clear fluid called "aqueous humor." Aqueous humor is formed in the posterior chamber of the eye by the ciliary body at a rate of about 2.5 microliters per minute. The fluid, which is made at a fairly constant rate, then passes around the lens, through the pupillary opening in the iris and into the anterior chamber of the eye. Once in the anterior chamber, the fluid drains out of the eye through two different routes. In the "uveoscleral" route, the fluid percolates between muscle fibers of the ciliary body. This route accounts for approximately ten percent of the aqueous outflow in humans. The primary pathway for aqueous outflow in humans is through the "canalicular" route that involves the trabecular meshwork and Schlemm's canal.

The trabecular meshwork and Schlemm's canal are located at the junction between the iris and the sclera. This junction or corner is called "the angle." The trabecular meshwork is a wedge-shaped structure that runs around the circumference of the eye. It is composed of collagen beams arranged in a three-dimensional sieve-like structure. The beams are lined with a monolayer of cells called trabecular cells. The spaces between the collagen beams are filled with an extracellular substance that is produced by the trabecular cells. These cells also produce enzymes that degrade the extracellular material. Schlemm's canal is adjacent to the trabecular meshwork. The outer wall of the trabecular meshwork coincides with the inner wall of Schlemm's canal. Schlemm's canal is a tube-like structure that runs around the circumference of the cornea. In human adults, Schlemm's Canal is believed to be divided by septa into a series of autonomous, dead-end canals.

The aqueous fluid travels through the spaces between the trabecular beams, across the inner wall of Schlemm's canal into the canal, through a series of about 25 collecting channels that drain from Schlemm's canal and into the episcleral venous system. In a normal situation, aqueous production is equal to aqueous outflow and intraocular pressure remains fairly constant in the 15 to 21 mmHg range. In glaucoma, the resistance through the canalicular outflow system is abnormally high.

In primary open angle glaucoma, which is the most common form of glaucoma, the abnormal resistance is believed to be along the outer aspect of trabecular meshwork and the inner wall of Schlemm's canal. It is believed that an abnormal metabolism of the trabecular cells leads to an excessive build up of extracellular materials or a build up of abnormally "stiff" materials in this area. Histopathology of glaucoma eyes also demonstrates a collapse of Schlemm's canal. Primary open angle glaucoma accounts for approximately eighty-five percent of all glaucoma. Other forms of glaucoma (such as angle closure glaucoma and secondary glaucomas) also involve decreased outflow through the canalicular pathway but the increased resistance is from other causes such as mechanical blockage, inflammatory debris, cellular blockage, etc.

With the increased resistance, the aqueous fluid builds up because it cannot exit fast enough. As the fluid builds up, the intraocular pressure (IOP) within the eye increases. The increased IOP compresses the axons in the optic nerve and also may compromise the vascular supply to the optic nerve. The optic nerve carries vision from the eye to the brain. Some optic nerves seem more susceptible to IOP than other eyes. While research is investigating ways to protect the nerve from an elevated pressure, the only therapeutic approach currently available in glaucoma is to reduce the intraocular pressure.

The clinical treatment of glaucoma is approached in a step-wise fashion. Medication often is the first treatment option. Administered either topically or orally, these medications work to either reduce aqueous production or they act to increase outflow. Currently available medications have many serious side effects including: congestive heart failure, respiratory distress, hypertension, depression, renal stones, aplastic anemia, sexual dysfunction and death. Compliance with medication is a major problem, with estimates that over half of glaucoma patients do not follow their correct dosing schedules.

When medication fails to adequately reduce the pressure, laser trabeculoplasty often is performed. In laser trabeculoplasty, thermal energy from a laser is applied to a number of noncontiguous spots in the trabecular meshwork. It is believed that the laser energy stimulates the metabolism of the trabecular cells in some way, and changes the extracellular material in the trabecular meshwork. In approximately eighty percent of patients, aqueous outflow is enhanced and IOP decreases. However, the effect often is not long lasting and fifty percent of patients develop an elevated pressure within five years. The laser surgery is not usually repeatable. In addition, laser trabeculoplasty is not an effective treatment for primary open angle glaucoma in patients less than fifty years of age, nor is it effective for angle closure glaucoma and many secondary glaucomas.

If laser trabeculoplasty does not reduce the pressure enough, then filtering surgery is performed. With filtering surgery, a hole is made in the sclera and angle region. This hole allows the aqueous fluid to leave the eye through an alternate route.

The most commonly performed filtering procedure is a trabeculectomy. In a trabeculectomy, a posterior incision is made in the conjunctiva, the transparent tissue that covers the sclera. The conjunctiva is rolled forward, exposing the sclera at the limbus. A partial thickness scleral flap is made and dissected half-thickness into the cornea. The anterior chamber is entered beneath the scleral flap and a section of deep sclera and trabecular meshwork is excised. The scleral flap is loosely sewn back into place. The conjunctival incision is tightly closed. Post-operatively, the aqueous fluid passes through the hole, beneath the scleral flap and collects in an elevated space beneath the conjunctiva. The fluid then is either absorbed through blood vessels in the conjunctiva or traverses across the conjunctiva into the tear film.

Trabeculectomy is associated with many problems. Fibroblasts that are present in the episclera proliferate and migrate and can scar down the scleral flap. Failure from scarring may occur, particularly in children and young adults. Of eyes that have an initially successful trabeculectomy, eighty percent will fail from scarring within three to five years after surgery. To minimize fibrosis, surgeons now are applying antifibrotic agents such as mitomycin C (MMC) and 5-fluorouracil (5-FU) to the scleral flap at the time of surgery. The use of these agents has increased the success rate of trabeculectomy but also has increased the prevalence of hypotony. Hypotony is a problem that develops when aqueous flows out of the eye too fast. The eye pressure drops too low (usually less than 6.0 mmHg); the structure of the eye collapses and vision decreases.

Trabeculectomy creates a pathway for aqueous fluid to escape to the surface of the eye. At the same time, it creates a pathway for bacteria that normally live on the surface of the eye and eyelids to get into the eye. If this happens, an internal eye infection can occur called endophthalmitis. Endophthalmitis often leads to permanent and profound visual loss. Endophthalmitis can occur anytime after trabeculectomy. The risk increases with the thin blebs that develop after MMC and 5-FU. Another factor that contributes to infection is the placement of a bleb. Eyes that have trabeculectomy performed inferiorly have about five times the risk of eye infection than eyes that have a superior bleb. Therefore, initial trabeculectomy is performed superiorly under the eyelid, in either the nasal or temporal quadrant.

In addition to scarring, hypotony and infection, there are other complications of trabeculectomy. The bleb can tear and lead to profound hypotony. The bleb can be irritating and can disrupt the normal tear film, leading to blurred vision. Patients with blebs generally cannot wear contact lenses. All of the complications from trabeculectomy stem from the fact that fluid is being diverted from inside the eye to the external surface of the eye.

When trabeculectomy doesn't successfully lower the eye pressure, the next surgical step often is an aqueous shunt device. An aqueous shunt device of the prior art is a silicone tube that is attached at one end to a plastic (polypropylene or other synthetic) plate. With an aqueous shunt device, an incision is made in the conjunctiva, exposing the sclera. The plastic plate is sewn to the surface of the eye posteriorly, usually over the equator. A full thickness hole is made into the eye at the limbus, usually with a needle. The tube is inserted into the eye through this hole. The external portion of the tube is covered with either donor sclera or pericardium. The conjunctiva is replaced and the incision is closed tightly. Many problems exist with the current technology of aqueous shunt devices including scarring, failure, hypotony, and infection.

Some prior art references for glaucoma management have been directed at Schlemm's canal, but these have not involved the placement of long-term, indwelling stents. For example, U.S. Pat. No. 5,360,399 teaches the placement of a portion of a plastic or steel tube in Schlemm's canal with injection of a viscous material through the tube to hydraulically dissect the trabecular meshwork. The tube is removed from the canal following injection. Furthermore, relative to that portion within Schlemm's canal, the '399 device has a larger diameter injection cuff element, which serves as an adapter for injection and irrigation. Therefore, this device is not adapted for permanent placement within Schlemm's canal.

A need exists, then, for a more physiologic system to enhance the drainage of aqueous fluid through Schlemm's canal. Enhancing aqueous flow directly into Schlemm's canal would minimize scarring since the angle region is populated with a single line of nonproliferating trabecular cells. Enhancing aqueous flow directly into Schlemm's canal would minimize hypotony since the canal is part of the normal outflow system and is biologically engineered to handle the normal volume of aqueous humor. Enhancing aqueous flow directly into Schlemm's canal would eliminate complications such as endophthalmitis and leaks.

SUMMARY OF THE INVENTION

The present invention is directed to a novel stent and an associated surgical method for the surgical correction of glaucoma in which the stent is placed into Schlemm's canal to expand the canal's dimensions and maintain its patency. The present invention therefore facilitates the normal physiologic pathway for drainage of aqueous humor into and through Schlemm's canal. The present invention is further directed to providing a permanent, indwelling stent within Schlemm's canal for glaucoma management.

DETAILED DESCRIPTION OF PRESENT INVENTION

The present invention provides an aqueous humor stent device to be placed within a portion of Schlemm's canal of the eye as an indwelling implant to expand and maintain the patency of the canal, in which the stent device comprises a body portion shaped to be wholly received within Schlemm's canal to facilitate the natural drainage of aqueous humor to the collecting channels of the eye.

The present invention also provides embodiments of an inventive stent comprising a thin body of biocompatible material of a length and shape adapted to be wholly received within Schlemm's canal and to extend within a portion of the circumference of Schlemm's canal, and having a channel therein to facilitate the passage of aqueous humor into and through Schlemm's canal to the collecting channels. The invention contemplates many different configurations for a stent device, provided that each assists in channeling aqueous humor throughout Schlemm's canal, such as by providing a lumen, trough, wick or capillary action. In some embodiments of the invention, the body of the stent can move between a first insertion position and a second expanded stenting position when in a desired location of the canal.

The present invention also provides methods of use of the stent devices. One embodiment of the present invention is directed to a surgical method to implant the inventive stent into a portion of the circumference of Schlemm's canal. The device extending into Schlemm's canal may be fashioned from a flexible, porous or non-porous, biologically inert material to approximately equal a portion of the radius, curvature, and diameter of Schlemm's canal. All or parts of the device may be tubular or non-tubular, and fenestrated or non-fenestrated. The device may further be sized to allow placement through all or some of the circumference of Schlemm's canal.

Traditional glaucoma teaching states that Schlemm's canal in an adult is divided by septa into separate canals, rendering the complete passage of a suture impossible. Preliminary studies on adult human eye bank eyes have shown that Schlemm's canal is, indeed, patent. A suture can be passed through the entire circumference of the canal. It has not been heretofore determined that Schlemm's canal is patent throughout its circumference in normal individuals, as opposed to being divided by septa into multiple dead end canals. The present invention utilizes this knowledge to create and maintain patency within Schlemm's canal with the present stent devices.

Figure 1:
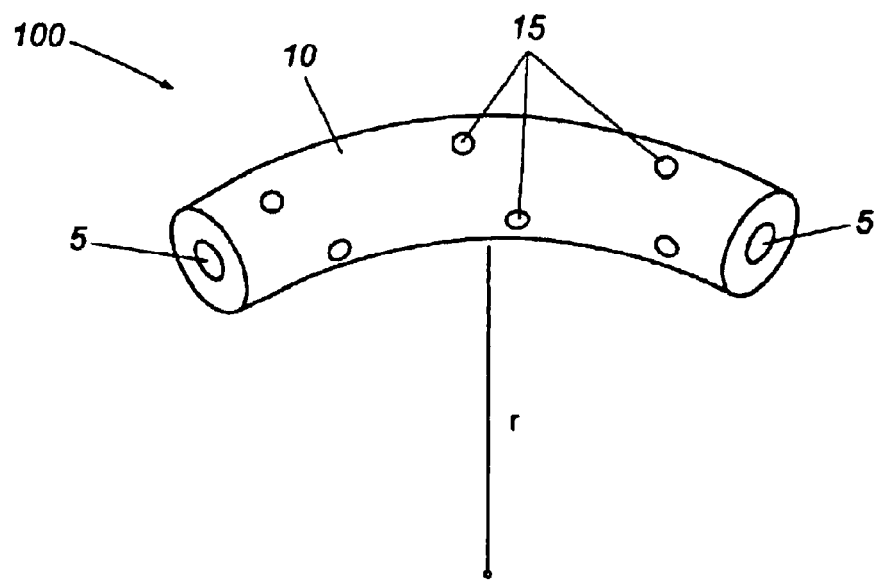
FIG. 1 is an illustration showing a side view of one embodiment of the present invention, in which the inventive stent is comprised of tubular elements traversing the circumference of Schlemm's canal.

One embodiment of the present invention is illustrated in FIG. 1, in which the stent device 100 is shown in a side view. The stent device 100 is comprised of a tubular body portion 10 defining a lumen 5 which may have solid tubular walls or may contain a plurality of fenestrations 15 communicating between the lumen 5 and the exterior. The body portion has a pre-formed curvature with a radius r which approximates the 6 mm radius of Schlemm's canal of an adult human eye. The cross-sectional diameter of the body portion 10 is sized to be fully received within Schlemm's canal. The body portion 10 may be either an enclosed tubular or multisided structure, or it may be a flat, angular, or curved open structure, or some combination of the above when cross-sectioned at different sites along the entirety of its length. The fenestrations 15 may be placed along any portion of the device 100 to facilitate the passage of fluid therethrough.

Figure 2:
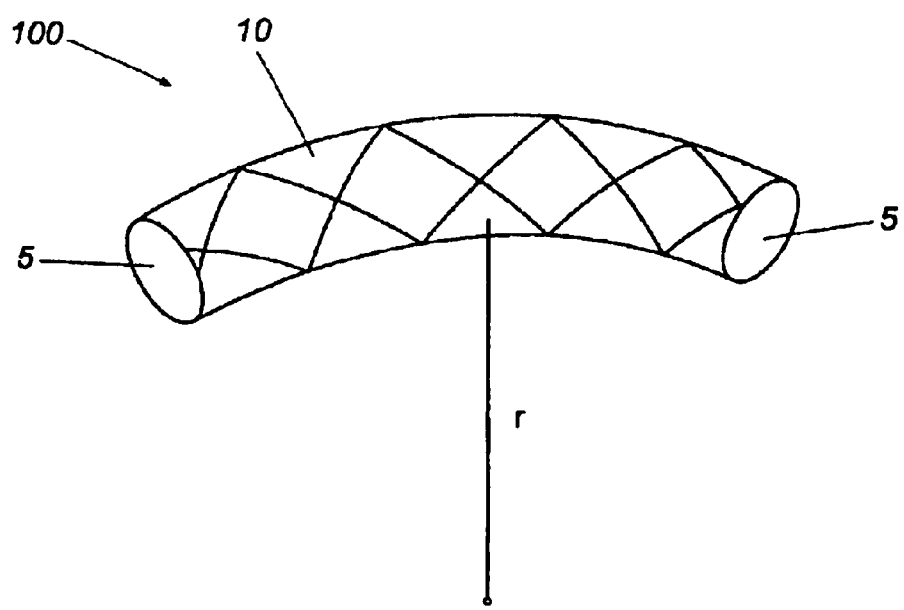
FIG. 2 is an illustration showing another embodiment of the present invention, in which the inventive stent is comprised of luminal mesh tubular elements.
Figure 3:
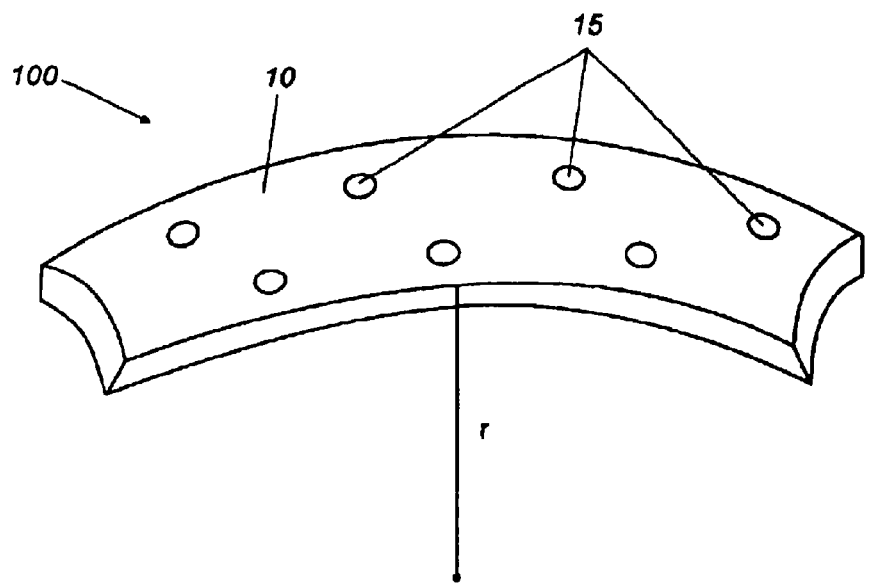
FIG. 3 is an illustration showing another embodiment of the present invention in which the inventive stent is comprised of elements that are partially tubular and partially open in their configuration.

Other examples of embodiments of the present invention are shown in FIGS. 2–3. FIG. 2 shows an embodiment of the inventive stent in which the device 100 comprises a luminal tubular mesh in its configuration, again with a pre-formed curvature with a radius r to approximate the 6 mm radius of Schlemm's canal and a cross-sectional diameter of the body portion 10 sized to be fully received within Schlemm's canal.

FIG. 3 shows an embodiment of the inventive stent in which the body portion 10 is open and curved throughout its length in a trough-like channel, again with a pre-formed curvature with a radius r to approximate the 6 mm radius of Schlemm's canal and a cross-sectional diameter of the body portion 10 sized to be fully received within Schlemm's canal.

As the inventive device is a long-term implant, it can be fabricated from a material that will be innocuous to the tissues and fluids with which it is in contact. It is preferable that the device not be absorbed, corroded, or otherwise structurally compromised during its in situ tenure. Moreover, it is equally preferable that the eye tissues and the aqueous remain non-detrimentally affected by the presence of the implanted device. A number of materials are available to meet the engineering and medical specifications for the stents. In the exemplary embodiments of the present invention, the stent device 100 is constructed of a biologically inert, flexible material such as silicone or similar polymers. Alternate materials might include, but are not limited to, thin-walled polytetrafluoroethylene, polypropylene or other polymers. Other metals and alloys known in the art of stenting can also be used, such as stainless steel, titanium or nitinol. The stent can also be fabricated with therapeutic agents that migrate from the device over time.

In the embodiments shown in FIGS. 1–5, the body portion 10 may have a pre-formed curve to approximate the 6.0 mm radius of Schlemm's canal in a human eye. The body portion 10 may be of sufficient length to extend through any length of the entire circumference of Schlemm's canal, with a total length for the body portion 10 of about 1.0 mm to 40 mm, or about 2 mm to 20 mm, or about 5 mm to permit circumferential placement through Schlemm's canal. The diameter or width of the body portion 10 can be sized to yield an internal diameter of between 0.1 mm and 0.5 mm, preferably about 0.2 mm and an external diameter of between 0.1 mm and 0.5 mm, or about 0.3 mm, for a tubular or curved stent, or a comparable maximal width for a stent with a multiangular configuration. The body portion 10 may contain a plurality of fenestrations to allow fluid egress, arranged to prevent occlusion by the adjacent walls of Schlemm's canal, particularly in the direction of the collecting channels.

Figure 5:
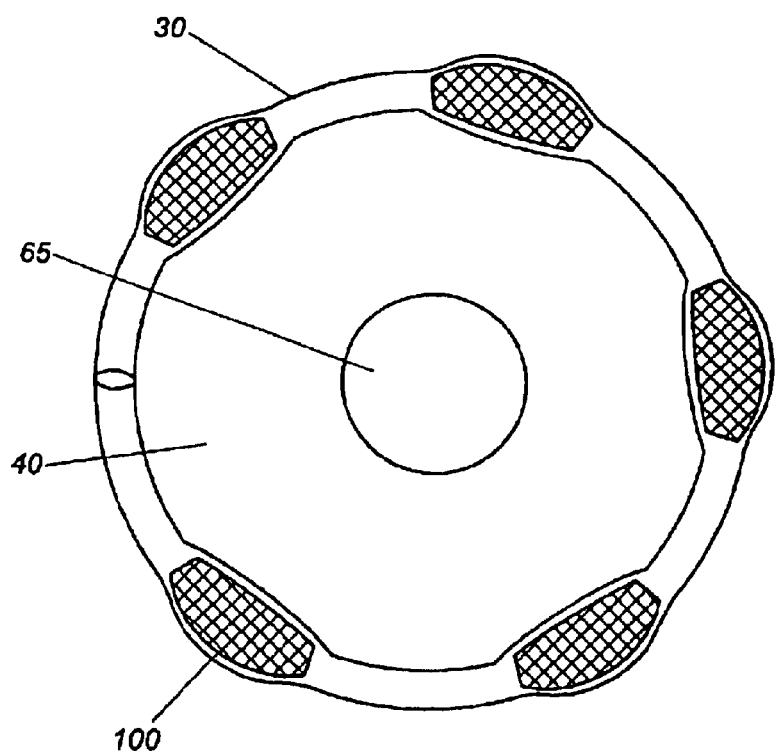
FIG. 5 is an illustration showing the anatomic relationships (not to scale) of the surgical placement of an exemplary embodiment of the present invention.
Figure 4:
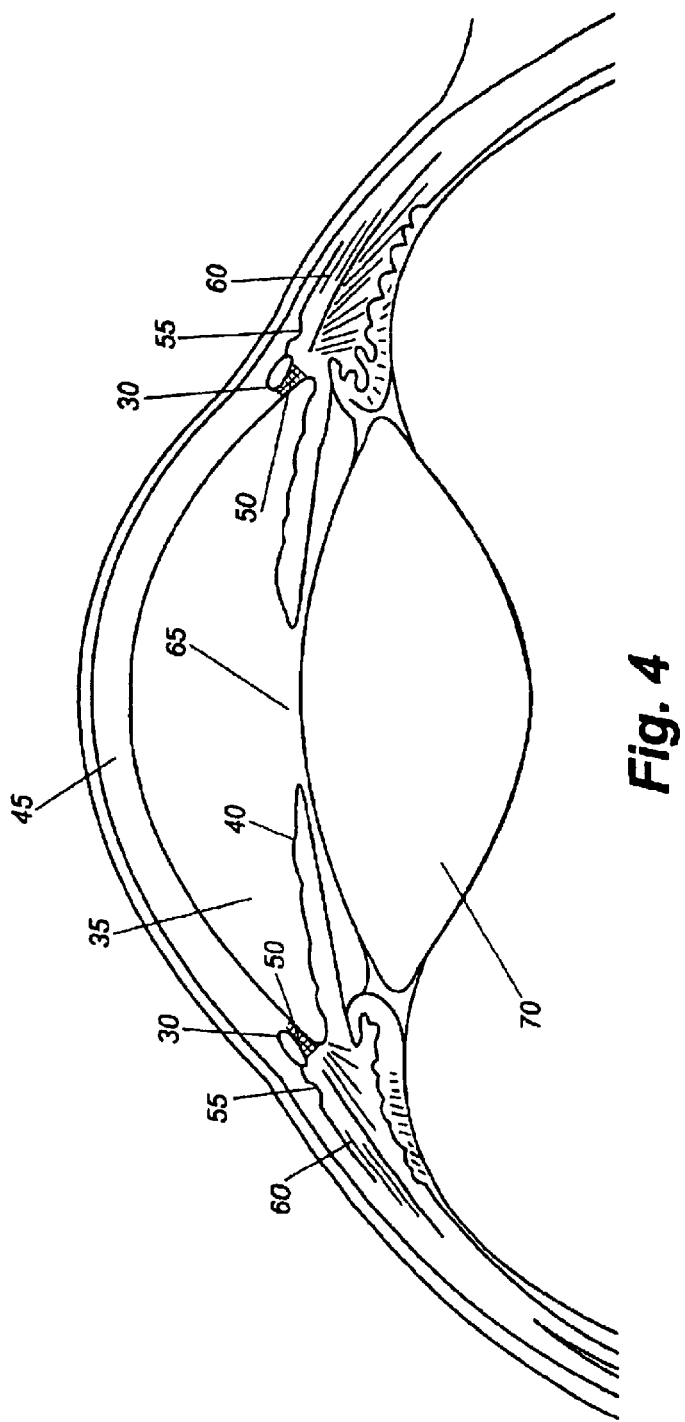
FIG. 4 is an illustration showing the anatomic details of the human eye.

The surgical anatomy relevant to the present invention is illustrated in FIG. 4. Generally, FIG. 4 shows the anterior chamber 35, Schlemm's canal 30, the iris 40, cornea 45, trabecular meshwork 50, collecting channels 55, episcleral veins 60, pupil 65, and lens 70. FIG. 5 illustrates the surgical placement of the exemplary embodiment of the present invention, with the relevant anatomic relationships. It should be noted that the inventive device is designed so that placement of multiple stents within Schlemm's canal 30 can result in a near-circumferential traverse of Schlemm's canal 30. The surgical incision into Schlemm's canal 30 is closed, with no direct external communication with the stent device 100 intended.

The surgical procedure necessary to insert the device may include all or some of the following steps: A conjunctival incision is made. A partial thickness scleral flap is then created and dissected half-thickness into clear cornea. The posterior aspect of Schlemm's canal is identified and the canal is entered posteriorly. The anterior chamber may be deepened with injection of a viscoelastic or miotid agent. A balloon catheter, such as described in U.S. Ser. No. 09/558,557, filed Apr. 26, 2000, may be introduced into Schlemm's canal, and inflated to dilate portions of Schlemm's canal, followed by the selective deflation of the balloon and placement of one or more stent devices into Schlemm's canal. Alternately, the stent devices may be introduced directly on a balloon catheter device. Therefore, a plurality of stent segments may be placed at selected locations along the circumference of Schlemm's canal. Any residual stent material is trimmed, and the scleral flap and conjunctival wound are closed in a conventional manner.

While the above-described embodiments are exemplary, the invention contemplates a wide variety of shapes and configurations of the stent to provide fluid communication between the anterior chamber and Schlemm's canal and to the collecting channels. The above-described embodiments are therefore not intended to be limiting to the scope of the claims and equivalents thereof.

What is claimed is:

1. A stent device for use in the eye to relieve excess intraocular pressure by facilitating drainage through and within Schlemm's canal in the eye, comprising a thin body of biocompatible material of a length and shape adapted to be wholly retained within a portion of Schlemm's canal, wherein said body is curved to define a trough-like, partially open channel along at least some of the length of said body open toward the collecting channels of the eye, said body has a width of about 0.1 mm to 0.5 mm, and said body has a length of about 1 mm to 40 mm.

2. The stent device of claim 1, wherein said body provides for drainage in both directions along Schlemm's canal.

3. The stent device of claim 1, wherein the body of the stent is at least partially luminal.

4. The stent device of claim 1, wherein said body has a curve having a radius which approximates the radius of Schlemm's canal of a human eye, wherein the radius is between about 3 mm and 10 mm.

5. The stent device of any of claims 1–4, wherein said body has a curve having a radius of about 6 mm.

6. The stent device of any of claims 1–4, wherein said body has an outer diameter of about 0.3 mm.

7. The stent device of any of claims 1–4, wherein said body has a length of about 20 mm.

8. The stent device of any of claims 1–4, wherein said body has a plurality of fenestrations therein that allow the passage of fluid into Schlemm's canal.

9. A method for the surgical treatment of glaucoma, comprising, performing a trabeculotomy through a conjunctival flap made at the limbus; developing a partial thickness scleral flap; radially incising the junction between the angle tissue and the sclera, which is surgically extended until Schlemm's canal is entered posteriorly, and placing one or more of the stent devices of any of claims 1–4 within Schlemm's canal.

* * * * *